United States Patent [19]

Stiles

[11] 4,131,616

[45] Dec. 26, 1978

[54] METHANATION CATALYST

[75] Inventor: Alvin B. Stiles, Wilmington, Del.

[73] Assignee: E. I. Du Pont de Nemours and Company, Wilmington, Del.

[21] Appl. No.: 482,574

[22] Filed: Jun. 24, 1974

[51] Int. Cl.² ............................................. C07C 27/06
[52] U.S. Cl. ........................ 260/449.6 M; 260/449 M; 260/449 S
[58] Field of Search ............. 260/449.6, 449 M, 449 S

[56] References Cited

U.S. PATENT DOCUMENTS 2,685,596   8/1954   Buchmann ........................ 260/449 S

OTHER PUBLICATIONS

Mills et al, "Catalysis Reviews" 8 (2), 189–195, (1973).

*Primary Examiner*—A. Siegel

[57] ABSTRACT

An improved nickel chromite catalyst useful for methanation is prepared by pre-reducing the hexavalent chromium component thereof to trivalent form, while maintaining the nickel component in unreduced oxide form.

2 Claims, No Drawings

METHANATION CATALYST

BACKGROUND OF THE INVENTION

Field of the Invention

The invention relates to an improved catalyst composition useful for carrying out the methanation of carbon oxides. More particularly, the invention relates to improved nickel chromite catalysts for this use.

Description of the Prior Art

The manufacture of synthesis gases or gaseous fuels from gaseous, liquid and solid carbonaceous materials is, of course, well-known and practiced widely throughout the world. Such gaseous products, which may be referred to as water gas, blue gas, blow run gas or simply as synthesis gas, are produced by the reaction of such hydrocarbons with water, oxygen or mixtures thereof to form a mixture of carbon monoxide, hydrogen and carbon dioxide. Such gaseous mixtures are useful not only as fuels, but also as a source of hydrogen and synthesis gases for methanol or ammonia. These gas mixtures are also useful for the synthesis of gaseous hydrocarbons, though their use in this manner has heretofore been largely uneconomical. Nevertheless, in view of the relatively large quantities of solid carbonaceous materials available in many countries as compared with the relatively limited quantities of liquid fossil fuels and the rising costs of both fuels and raw materials derived from liquid fossil fuels, the use of solid fuels as a source of gaseous mixtures for the synthesis of petrochemicals is fast becoming more feasible from an economic viewpoint and is likely to be of vital economic importance in the future.

An important reaction when water gas and/or synthesis gas is to be used for petrochemicals synthesis is the so-called methanation reaction by which mixtures of hydrogen and nitrogen contaminated with carbon monoxide and/or carbon dioxide are purified by converting their contaminants to methane and water in the presence of certain heterogeneous catalytic materials. This step is normally conducted at a temperature between 200° and 400° C. and under pressures between 100 and 500 p.s.i., by passing the feed gas over a Group VIII metal, particularly nickel, iron, cobalt and ruthenium or mixtures thereof, containing a suitable activator-stabilizer such as chromium oxide, aluminum oxide or thorium oxide.

In the past, an important catalyst for methanation has been nickel deposited on an alumina carrier. However, this catalyst has the disadvantage that it has a quite high threshold temperature and, furthermore, is very sensitive to the presence of sulfur contaminants which are frequently present in carbonaceous raw materials, particularly coal, from which the synthesis gas is derived. Because such catalysts are so easily poisoned by even small amounts of sulfur compounds, it is frequently necessary to precede the methanation reaction by a separate sulfur removal step (guard reactor) in which sulfur is removed by passing the sulfur-containing gas over a catalyst-chemisorbant such as reduced copper, copper oxide, carbon, zinc oxide, copper-zinc oxides, iron oxide, iron oxide plus alkali, etc. A still further disadvantage of the nickel-on-alumina catalyst is that it is thermally unstable, i.e. tends to become deactivated by exposure to high operating temperatures.

Another quite effective methanation catalyst is nickel chromite. This catalyst typically has a mol ratio of nickel to chrominum of about 1:1. This catalyst may be prepared by precipitating basic nickel ammonium chromate from a hot solution of nickel nitrate and chromic acid by the addition of anhydrous ammonia. The precipitate is filtered, washed, ignited either with or without prior drying and the ignited powder kneaded to obtain a dense paste. The kneaded paste is then dried, granulated and the granulated powder mixed with a lubricant such as graphite or a vegetable stearate in amounts ranging from 0.5 to 5.0% based on the weight of powder. This mixture is then pilled to the desired size. In this form it is ready for positioning in the converter in which the methanation reaction is conducted.

However, before such nickel catalyst can be used in the methanation reaction, it is necessary that it be reduced, i.e. the hexavalent chromium is converted to trivalent chormium and the nickel oxide is converted to elemental nickel. This has heretofore been accomplished by exposing the catalyst to an inert atmosphere at elevated temperatures for a prolonged period during which a small amount of hydrogen is bled into the inert atmosphere to effect reduction of the catalyst. Because the inert gas, usually nitrogen, must be heated indirectly, it is obvious that special heat transfer means have to be employed. Moreover, this method of reduction results in the catalysts being converted to a pyrophoric form, which necessitates that it be kept from oxygen-containing atmospheres to avoid spontaneous reoxidation, a self-destructive reaction.

The reduction procedure is very sensitive to hydrogen concentration. Because of the tremendous exotherm produced by the reduction of hexavalent chromium to trivalent chromium, even residual amounts of hexavelent chromium in the catalyst will result in loss of activity or even fusing of the catalyst if the reduction is not carried out with extensive dilution of the reducing gas. To avoid this excessive isotherm, the reducing gas must be diluted to an extent that it contains no more than about 1 mol % reducing gas and at least about 99 mol % inert gas(es). Furthermore, notwithstanding such extensive dilution, the reduction procedure must be performed quite slowly and therefore may extend up to several days.

Thus, the catalyst requires quite long and special and therefore expensive handling procedures and equipment. For this reason, despite the superiority of nickel chromite catalyst for methanation, its use is frequently rejected in favor of the less effective nickel/alumina catalyst which does not require such expensive preparation and handling procedures prior to use.

SUMMARY OF THE INVENTION

The disadvantages of the prior art nickel chromite catalyst have now been overcome by the invention which is an improved nickel chromite catalyst, the hexavalent chromium content in which has been pre-reduced to trivalent form while maintaining the nickel therein in unreduced oxide form prior to use. The resultant catalyst is more active, has longer life and is more resistant to poisons than the aforementioned nickel on alumina. Because the catalyst is stable and non-pyrophoric, it can be safely and conveniently handled and stored without special procedures. Furthermore, because there is no exotherm produced upon reducing nickel oxide with hydrogen, the catalyst of the invention can be introduced directly into the feed gas stream without prior reduction and reduced in situ at normal methanation operating conditions.

DETAILED DESCRIPTION OF THE INVENTION

In one aspect, the invention is directed to the method of making an improved nickel chromite catalyst suitable for the methanation of carbon oxides comprising the steps:

a. preparing an aqueous solution of compounds of the metals nickel and chromium in which solution the mol ratio of nickel to chromium is from about 0.5 to about 5.0;

b. adjusting the pH of the aqueous solution by which the metals are coprecipitated and separated from solution in finely divided solid form;

c. calcining and particulating the coprecipitated solids by which they are converted to an incipient crystalline compound containing a minor amount of hexavalent chromium ions; and d. reducing the hexavalent chromium ions contained in the incipient crystalline compound to trivalent form while maintaining the nickel in unreduced oxide form.

Suitable nickel compounds for use in the invention are nickel salts such as the nitrate, sulfate, chloride, formate or acetate, of which nickel nitrate is preferred since it yields a more active catalyst species in this application.

Suitable chromium compounds include hexavalent chromium compounds such as chromic acid anhydride ($CrO_3$), ammonium chromate or dichromate, trivalent chromium compounds such as potassium chromium sulfate [$K_2(CrSO_4)_2 \cdot XH_2O$], chromium acetate and formate and chromic chloride ($CrCl_3$). The chloride salt, though suitable in making the catalyst of the invention, is not preferred for the reason that chloride ion is objectionable in the final catalyst and must be removed from the precipitate. This is accomplished with great difficulty and requires extra washing steps.

In preparing the aqueous solution of the nickel and chromium compounds, it is preferred that the solution be rather dilute in order to favor the production of an intimate dispersion of quite small crystallites.

The nickel and chromium are coprecipitating from solution by addition of a suitable precipitating agent such as anhydrous ammonia, ammonium hydroxide, ammonium bicarbonate, ammonium carbonate, sodium carbonate, sodium bicarbonate and the carbonate or hydroxide of the other alkali metals (Li, K). Of the aforementioned precipitating agents, ammonium hydroxide is preferred. It is not only highly effective and inexpensive, but it has the additional advantage that it can readily be eliminated from the precipitate by heating during the calcining operation.

The precipitation step can be carried out over the pH range of from about 6.0 to about 8.0. However, incomplete precipitation may occur near the extremes of this range. For this reason it is preferred to carry out the precipitation step at pH 6.4–7.2. When the precipitation proceeds by metathesis, as would be the case when using ammonium hydroxide or carbonates to coprecipitate hexavalent chromium and complex nickel, the precipitate is a complex in which the ions therein are bonded, albeit loosely. On the other hand, when the precipitation proceeds without metathesis, as would be the case when using ammonium hydroxide or carbonate to coprecipitate chromium and nickel hydroxy carbonates, the coprecipitate is merely an intermixture of the respective hydroxides or carbonates of nickel and chromium. In either case, however, the fineness and high degree of dispersion of the metal precipitates is quite important to the efficacy of the catalyst produced therefrom.

Increased stability of the catalyst can be obtained by coprecipitating with the basic nickel chromate complex an interspersant such as aluminum hydroxide derived from finely divided (0.1–10 micron) aluminum nitrate, alumina hydrate or aluminum oxide, chromic oxide, ($Cr_2O_3$), chromium hydroxide, cerium oxide or carbonate, magnesium oxide, mixed rare earth oxides or carbonates, alkali earth oxides or silica. These can acceptably be added as the oxides, hydroxides, carbonates, basic carbonates, or can be added as soluble salts, and be coprecipitated with the basic nickel chromate complex as the hydroxides or carbonates. These can be added to the extent of 0.5% to as much as 75% of the total weight of the finished catalyst. The stabilizing effect is increased by increasing the quantity, but the inherent activity of the catalyst is decreased by the diluting effect of the stabilizers.

It is important that the coprecipitate, whether an intermixture or a complex, be calcined in such manner as to form crystallites which are amorphous to X-rays. This form of the calcined coprecipitate may be characterized as a complex incipiently crystalline compound which is inherently a spinel. However, this characteristic is not identifiable until the compound is heated to a higher temperature, e.g. 500° C. or above, at which the crystallites grow to a size readily identifiable by X-rays as spinel. This precise structure - an amorphous, incipient spinel - has been found to give a high degree of catalytic activity and stability, is obtained by heating the coprecipitated solids dispersion to a temperature of 275–600° C. and preferably 350–450° C. in a non-reducing atmosphere.

Under these conditions, the resultant incipiently crystalline compound is found to contain mainly trivalent chromium but also a minor amount, e.g. from about 0.3 to about 3% by weight, of hexavalent chromium. It is of interest that the amount of hexavalent chromium present in the calcined coprecipitate is of the same order of magnitude whether derived from trivalent or hexavalent chromium sources. Thus, when the coprecipitate is derived from trivalent chromium, a small amount (0.3–1.5% by weight) of hexavalent chromium is formed during calcination. Conversely, when the coprecipitate is derived from hexavalent chromium, most of the hexavalent chromium is reduced to trivalent form, however, a small amount (0.8–3% by weight) remains. A further important characteristic of the incipiently crystalline compound is that the unreduced nickel oxide contained therein is incompletely soluble in strong mineral acids, such as nitric and hydrochloric acids, whereas nickel oxide in any other environment is known to be completely soluble in such acids. This phenomenon is, of course, indicative that the nickel oxide is at least in part intimately combined in the incipiently crystalline structure which results from calcination.

An appropriate non-reducing atmosphere is obtained by utilizing any of several neutral or oxidizing gases or gas mixtures, e.g. nitrogen, helium, oxygen and air. It is important that the upper temperature limit of about 500° C. not be exceeded for any substantial time since prolonged exposure above 500° C. will change the incipient crystalline structure and thus lower the activity level of the catalyst made therefrom. Temperatures to 600° C. may be utilized on a very limited basis; however, exposure for longer than 2 to 15 minutes will result in crystallite growth and partial deactivation of the catalyst.

It will be preferred to utilize the catalyst of the inventional in particulate form. This form is attained by either of two ways: (1) by depositing the catalyst on a suitable particulate carrier; and (2) by particulating the catalyst, e.g. by pilling, extrusion or granulation. Any of these methods of particulation may be performed on the calcined or uncalcined catalyst solids. When the catalyst is to be particulated without using a support, it is preferred to carry out the particulation after calcination. On the other hand, when preparing the catalyst by impregnation on a carrier or support, it is preferred to calcine the catalyst following impregnation.

Suitable catalyst supporting materials include granules (including pellets) of alumina, of all crystallite species, e.g. alpha, gamma, chi, etc., silica-alumina, mullite and sillimanite. Other appropriate materials will be apparent to those who are skilled in the art of catalyst formulation.

A particularly important step of the process by which the catalyst of the invention is prepared is the reduction of the catalyst prior to use. As mentioned hereinabove, an outstanding feature of the catalyst of the invention is that it may safely and conveniently be handled even in open air and yet it does not require any special startup procedures when it is charged to a reactor and brought on stream for the methanation reaction. To accomplish this, it is necessary that the hexavalent chromium content of the catalyst be converted to the trivalent form while maintaining the nickel component thereof in unreduced oxide form. This quite crucial step is accomplished by treating the calcined catalyst with a reducing gas at a temperature of 100–300° C. depending upon the pressure. At a pressure of atmospheric to about 10 p.s.i.g., the temperature may be as high as about 300° C. However, at elevated pressures, e.g. 10–1000 p.s.i.g., the temperature of reduction must be maintained below 300° C., preferably below about 250° C. in order to avoid incipient reduction of the nickel oxide and the resultant formation of pyrophoricity in the catalyst.

Suitable reducing gases include hydrogen, carbon monoxide and mixtures thereof with various inert gases. However, the use of carbon monoxide is not preferred because it tends under certain known conditions of pressure and temperature to favor the formation of nickel pentacarbonyl from a portion of the nickel oxide present. Thus, hydrogen is preferred as the reducing gas.

To minimize sudden physical stresses and to avoid severe exotherms, it is preferred to treat the non-reduced catalyst with a quite dilute concentration of reducing gas and then to use a higher concentration when reduction nears completion. Reduction of the hexavalent chromium is evidenced by the evolution of water vapor from the catalyst. Thus, so long as water can be detected in the reducing gas outlet, the catalyst remains incompletely reduced. When reduction appears completed as shown by the absence of any further water evolution at the above-referred conditions of pressure and temperature, the hydrogen content of the reducing gas is then increased stepwise up to a level of 100% hydrogen. At that level, if no water vapor is observed in the off-gas, the reduction of the chromate is deemed fully completed. Water vapor from the reducing step can be quite readily detected by passing a slip stream of the off-gas through a freezing trap at −40° C. or lower and observing whether or not any frost is formed.

As explained above, it is essential that the temperature of the catalyst during the reduction step not exceed about 300° C. at low reduction pressures and about 250° C. if higher pressures are used since at those temperatures, reduction of the nickel oxide in the catalyst takes place by which the catalyst will be rendered pyrophoric if the extent of reduction is sufficient. However, a temperature of at least about 100° C. is necessary to obtain sufficient speed of reaction and to remove water from the catalyst system.

Once the chromium is reduced in the above-described manner, the catalyst can safely and easily be handled by conventional solids handling procedures without regard to air exposure. Thus, depending upon the particular form of the catalyst it may be charged to the methanation reactor from drums or by pneumatic means and immediately placed in operation at methanating conditions of pressure, temperature and gas composition. By contrast, when conventional nickel chromite catalysts are used, they require quite careful reduction over a period of several hours up to 2–4 days by circulating heated nitrogen gas containing successively higher concentrations of hydrogen over the catalyst until both the chromium is reduced to trivalent form and the nickel is fully reduced to the active metal form.

The catalyst of the invention is quite stable both physically and chemically, thus it can be used with a wider range of operating conditions as to temperature and pressure. Morever, because of its unusually high activity, it may be used at very high space velocities. An important characteristic of the catalyst of the invention is its very low threshold temperature for the methanation reaction. Unlike the conventional nickel/alumina catalyst which requires a temperature of at least about 300° C., the invention catalyst can be used effectively at temperatures as low as about 240° C. Such lower threshold temperature is particularly important in that it enables significantly higher CO feed concentrations to be used without incurring excessive exotherm, or, alternatively, smaller volumes of heat sink gas may be circulated to the process at a given reactor temperature. The catalysts can be used at temperatures up to about 700° C.; however, it is preferred to use temperatures on the order of 600° C. or below in order to minimize undesirable changes in the physical form of the catalyst which tend to render the catalyst less active, resulting in a raising of the threshold temperature. Still lower temperatures are preferred, e.g. 500° C. and still more preferably 400° C. or below, to maintain a reaction equilibrium more favorable to production of methane.

The methanation pressure is not critical. Thus, the process may be carried out at atmospheric pressure or, in theory, even below. Likewise, the process can be carried out at quite high pressures, e.g. 10,000 psia. Within these extremes, the choice of reaction pressure is primarily a matter of process and equipment economics. Pressures of from about 10 to about 5,000 psia will, however, be preferred for these reasons.

Because of the high degree of activity of the catalyst of the invention, the reactants may be contacted therewith at quite high space velocities. For example, at high pressures and temperatures (e.g. 5,000 psia and 500° C.), space velocities as high as 200,000 may be used depending on how low CO content is desired for the purified gas. At lower pressures and temperatures (e.g. 14.7 psia and 250° C.), space velocities as low as 500 may be required, again depending in part upon the desired degree of CO removal. A space velocity of from about 1,000 to about 50,000 is preferred. As used herein, the term "space velocity" refers to volumes of gas treated per hour per volume of catalyst.

In carrying out the methanation reaction on a commercial scale, appropriate steps must be taken to minimize the effects of the large exotherm produced by the reaction. For example, a 1% by volume increase of CO in the feed gas results in approximately a 75° C. increase in gas temperature. Thus, unless special steps are taken, the process is limited to quite small concentrations of CO lest the reaction temperature build up too high. In the past, this disadvantage has been alleviated by recirculating cooled product gases to the reaction.

While the above-described product recycle procedure is effective, it is nevertheless uneconomical at carbon oxide concentrations greater than about 5% by volume for the reason that the procedure increases the size requirement for both the converter and allied equipment such as pumps and compressors. Moreover, the energy requirements for the larger equipment are greater. Thus, this procedure is highly uneconomical for feed gases containing 20–25% by volume carbon oxides which would require that as much as 80% by volume of the effluent be recycled.

It is therefore a significant advantage of the unique catalyst of the invention that it can be used in such manner as to reduce substantially and/or even eliminate the necessity of recycling cooled effluent gases. Likewise, the catalyst can be used to increase the level of carbon oxides which can be treated while maintaining a given level of operating conditions.

In particular, to elaborate, costly and energy-wasteful procedures by which product gas is recycled are eliminated by the following described process in which feed gases containing quite high carbon oxide concentrations are treated in a plurality of methanating steps in the last stage of which the invention catalyst is used. The process employs the following sequence of steps:

(1) contacting a feed gas stream containing 3–25% by volume carbon oxides in hydrogen with a first stage methanation cataylst at a temperature between the threshold and deactivation temperatures of the catalyst by which a partially methanated gaseous reaction product is formed having an outlet temperature of 600–900° C.;

(2) cooling the first stage reaction product to 250–450° C.;

(3) contacting the cooled first stage reaction product containing a reduced amount of carbon oxides with at least one intermediate stage methanation catalyst at a temperature between the threshold and deactivation temperatures of the catalyst by which a further methanated gaseous reaction product is formed having an outlet temperature of 450–750° C.;

(4) cooling the intermediate stage reaction product to 200–400° C.; and (5) contacting the cooled intermediate stage reaction product containing a further reduced amount of carbon oxides with a final stage methanation catalyst comprising the catalyst of the invention at a temperature between the threshold and deactivation temperatures of the catalyst by which an essentially carbon oxide-free reaction product is formed having an outlet temperature of 375–600° C., the process being further characterized in that the gaseous reaction product outlet temperature in any stage is higher than for any succeeding stage.

In the above-described process, the initial and intermediate reaction stages are conducted at near equilibrium temperatures by which faster reaction rates are achieved and recoverable energy (from heat exchange) is maximized. Suitable first stage catalysts having a high deactivation temperature, include nickel oxide-nickel aluminate, supported nickel oxide and ruthenium. Nickel aluminate catalyst, including the catalyst of the invention, can also be used in the first stage provided that the deactivation temperature is not reached. In a preferred method of the operation, the catalyst of the invention is used in the lower temperature initial section of the catalyst bed while a heat resistant catalyst is used downstream where the temperature is much higher.

(6) In the final catalyst stage, the process is carried out under quite mild conditions by which the small carbon oxide content of the intermediate stage reaction product is essentially completely converted to methane. Using the above-described process, hydrogen-containing gases containing even quite high concentrations of carbon oxides may be purified to remove all but a few parts per million of CO and $CO_2$. For example, carbon oxide levels may be reduced to as low as 2–5 ppm by volume.

The invention will be more thoroughly understood by reference to the following examples.

EXAMPLE 1

This example illustrates preparation of the catalyst of the invention without the use of a support.

1. A solution is prepared comprising 290 g. of nickel nitrate hexahydrate, 100 g. of chromic acid anhydride ($CrO_3$) and sufficient distilled water to provide 1000 ml. total solution volume.

2. While this solution is being rapidly agitated in a stainless steel or glass container, it is heated to 35° C.

3. While the solution is rapidly agitated anhydrous ammonia is bubbled into the solution below the surface at the rate of 1 g./min. until sufficient has been added for a pH of 6.8–7.2 to be attained.

4. Agitation is continued for an additional 30 min. and then the slurry is filtered.

5. The filter cake is washed with 1 liter of distilled water to remove soluble salts and excess chromic ion.

6. The filter cake is next dried at 125–150° C. and then is calcined at 450° C. for 2 hr. after reaching this temperature.

7. The finely divided calcined material is densified by placing in a laboratory size sigma-blade kneader to which sufficient distilled water is added to produce a dense paste after a period of 30 min. of kneading.

8. The kneaded paste is dried at 150° C. and thereafter is pulverized to 100% through a 10 mesh screen.

9. The powder obtained after passing through the 10 mesh screen is mixed with 0.75% finely divided, high purity graphite as a pilling lubricant for the subsequent operation.

10. The powder mixed with graphite is compressed into pellets which are 3/16 inch × 3/16 inch right cylinders having an apparent density of approximately 1.1 g/ml.

The catalyst is prepared for the methanation reaction by charging to a converter unit capable of withstanding pressures up to 10,000 psi and temperatures to 600° C. The vessel containing a bed of the catalyst is equipped with an inlet gas line at one end and an exhaust line at the other and thermocouples are distributed through the catalyst bed.

The converter is surrounded on the outside by an electric heating coil which permits the obtaining of temperatures as high as the previously mentioned 600° C. A preheater for the gas is also provided which permits preheating the gas to a temperature as high as 400° C. before the gas reaches the catalyst.

With the external heat on and the converter and the inlet gas temperature both set at 250° C., a gas mixture comprising 2% hydrogen in nitrogen at atmospheric pressure is passed at an hourly space velocity of 5000 through the catalyst bed.

The gas entering the reactor is previously desiccated to remove water and prior to that any oxygen in the system is reacted over a platinum catalyst to convert it to water.

The gas passing through the catalyst bed reduces all chromate radical from a $Cr^{+6}$ state to $Cr^{+3}$; water is formed and passes out of the converter. Gas flow into the converter is continued until no water vapor is detectable in the exhaust line.

Water vapor is detected by passing the gas through a freezing trap at −40° C. or below to determine whether any frost will form in the trap. Reduction is continued until no moisture is obtained in the trap, at which point the hydrogen content of the gas is increased stepwise to 5%, 10%, 25%, 50% and 100%, checking each stage for the absence of reduction after a period of exposure of the catalyst to each specific hydrogen concentration. When no water vapor is obtained in the off-gas when 100% hydrogen is fed to the converter, the reduction of the chromate is considered complete.

The catalyst is removed after this reduction operation and is heated to 100° C. in air to determine that it has no pyrophoricity. A thermocouple is placed in a 2" diameter × 2" high conical pile of catalyst; when no exotherm is experienced it is evident that the reduced catalyst is suitable for being handled in air without the danger of overheating.

EXAMPLE 2

Use of the catalyst prepared in accordance with Example 1 for methanation is illustrated by this example.

The reduced catalyst is again charged to the converter and a gas comprising 1% carbon monoxide in hydrogen is charged to the converter. Inlet gas temperature is set at 400° C. and the jacket temperature is set at the same temperature. The rate of gas flow is set at 1000 space velocity.

Initially the hydrogen effected the reduction of the nickel oxide of the catalyst to elemental nickel, but as this progressed, the reaction of carbon monoxide with hydrogen to produce methane was increased. Eventually when all the nickel was reduced and the catalyst was in fully activated condition, carbon monoxide in the off-gas (carbon monoxide leakage) was reduced to less than 10 ppm, thus indicating the high efficiency of this catalyst for the methanation reaction.

The inlet gas and jacket temperatures were both decreased to 240° C. and similar removal of carbon monoxide was attained.

The space velocity was increased to 50,000 and the pressure was increased to 400 psi with the result that the exit gas contained less than 2 ppm CO.

The carbon monoxide content of the inlet gas was increased to 4% which occasioned a temperature rise within the converter of approximately 275° C. Thus the inlet gas temperature was 240° C. and the exit temperature was slightly over 500° C. Carbon monoxide leakage under these circumstances was less than 45 ppm.

Carbon monoxide content was increased to 5.5%, occasioning a temperature rise of approximately 375° C., bringing the temperature up to slightly over 600° C. Carbon monoxide leakage under these conditions was also close to equilibrium, being approximately 100 ppm. The catalyst after these tests was removed from the unit and was found to be extremely pyrophoric, reaching visible red heat when exposed to air and igniting paper on which the catalyst had been placed. This demonstrates the fact that catalyst in which both the Ni and Cr have been reduced is pyrophoric and therefore difficult to handle in air.

EXAMPLE 3

This example shows the effect of omitting the partial reduction step for preparing nickel chromate catalyst.

Using a fresh charge of pelleted catalyst made in accordance with steps 1–10 of Example 1, a new charge of catalyst is placed in the converter and is not given the preliminary reduction with the controlled hydrogen-nitrogen system, but instead the temperature is preheated to 400° C. and the jacket temperature is also maintained at 400° C., the inlet gas composition is 1% carbon monoxide in hydrogen. Pressure is maintained at atmospheric and space velocity is set at 1000.

As soon as the hydrogen-carbon monoxide mixture reached the catalyst at 400° C. the chromate portion of the catalyst immediately reduced and a very rapid temperature rise was encountered, the temperature reaching approximately 750° C. in approximately 30 sec. The hydrogen-carbon monoxide feed was continued until reduction was complete, as indicated by a drop-off in temperature to approximately 450° C.

At this temperature and this low gas feed, the carbon monoxide content of the exit gas was undesirably high, being 0.10% or 1000 ppm. This shows that the prior careful reduction not only stabilizes the catalyst for handling in air, but also eliminates its overheating when the catalyst is charged to a unit and is exposed to high concentrations of hydrogen.

When this catalyst was discharged it was smaller in diameter than when charged and also was different in color from the carefully reduced catalyst previously described. It was evident that great physical and catalytic change had occurred to the catalyst because of this uncontrolled reduction and high temperature exposure.

EXAMPLE 4

Catalyst as prepared in Example 1, steps 1–10 inclusively, is again charged to the unit. The catalyst is then heated externally to 250° C. and the inlet gas temperature is adjusted to the same temperature. Flow is set at 1000 space velocity and the inlet gas is set at a concentration of 2% hydrogen in nitrogen.

Reduction was effected at 250° C. until no moisture appeared in the exit gas as previously described to be the case. The temperature was next raised to 400° C. and the hydrogen concentration was increased to 100%. The catalyst had good activity for the methanation reaction.

A test of the pyrophoricity of this catalyst indicated that after the 400° C. reduction it was extremely pyrophoric, the temperature rising to red heat and again charring paper as described in Example 1.

EXAMPLE 5

A new charge of catalyst was reduced as described in the first two paragraphs of Example 4.

To determine whether this catalyst could be stabilized for exposure to air even after the 400° C. reduction, a steam flow of 1000 space velocity was passed over the catalyst at 400° C. for a period of 4 hours. Thereafter, the catalyst temperature was reduced to 35° C. and the catalyst was discharged to open air. There was no tendency for pyrophoricity. When the catalyst was recharged and immediately given a test for activity using the CO-hydrogen mixture, it was found that the activity after the steam treatment was equal to that obtained after the initial reduction as described in Example 4.

EXAMPLE 6

A catalyst was prepared as described in Example 1 with the exception that the chromium, instead of being added as chromic acid, was added as a stoichiometrically equivalent quantity of chromium nitrate.

Precipitation was effected to the same pH and a nickel hydroxide-chromium hydroxide intimate mixture was obtained.

This mixture was processed as described for Example 1 to the point where the pilled catalyst was obtained.

This catalyst contained less $Cr^{+6}$ because what $Cr^{+6}$ was present was derived only from oxidation during calcining. Consequently, the first stage reduction at 250° C. was of short duration. However, it was essential that this operation be performed because there was a harmful exothermal effect when high hydrogen concentrations were used. The catalyst after this first phase, low temperature reduction could be handled readily in air without any pyrophoricity being noted. Second stage reduction could be effected at 400° C. with essentially 100% hydrogen without any adverse exothermal effect.

Catalysts of this type after reduction gave high activity for the conversion of carbon monoxide in hydrogen to methane with low residual carbon monoxide in the gas stream.

Though in the process examples the catalysts were self-supporting, supported catalysts can be made in accordance with the invention by several different ways.

A preferred way is by dissolving nickel nitrate and chromium nitrate in water, impregnating alumina granules, for example, with the nitrates solution, drying and calcining the oxides. Concentration of the aqueous solution and the ratio of nickel:chromium can be varied through a wide range and a satisfactory catalyst still obtained. Instead of the chromium nitrate, chromic acid-ammonium chromate-nickel nitrate solution can also be used. Basic nickel chromate can be precipitated as described in Example 1 to the point of complete precipitation. This precipitate can then be dissolved either in excess chromic acid or in ammonium carbonate solution to effect a solution which can also be used to impregnate suitably selected granules.

The catalyst can be reduced and stabilized and reduced and activated by the aforementioned procedures to give a highly active catalyst for the methanation reaction.

A catalyst slurry suitable for use in either impregnated or unsupported catalysts can be made by reacting a slurry of nickel hydroxide or carbonate with chromic acid to give nickel chromate of a 1:1 Ni:Cr ratio or a mixture rich in Ni or $Cr^{+6}$. Use of the catalysts of the invention in a multistage converter or a series of converters is exemplified in the following example, in which all compositional percentages are by volume.

EXAMPLE 7

A gas ultimately to be converted to methane for high Btu substitute natural gas would ideally be composed of 75% hydrogen and 25% carbon monoxide or 80% hydrogen and 20% carbon dioxide. In actual practice a gas comprising hydrogen, carbon monoxide and carbon dioxide would be most likely to be used with a stoichiometric quantity of hydrogen being employed between the range of 75-80%, depending upon the ratio of $CO_2$ and CO. A greater proportion is needed if the proportion of carbon dioxide is increased. For the purpose of this example, a gas providing maximum exothermal heat of reaction (75% hydrogen, and 25% carbon monoxide) is methanated in a series of three converters. The first converter stage is charged with a high temperature resistant nickel oxide/nickel aluminate catalyst as well as a nickel chromite catalyst prepared in the manner of Example 1. The more temperature sensitive nickel chromite catalyst is located in the upstream part of the catalyst bed and the temperature resistant nickel oxide/nickel aluminate catalyst is located in the downstream part of the catalyst bed. A second and third stage converter are both charged with nickel chromite catalyst prepared in the manner of Example 1.

The above described mixture of hydrogen and carbon monoxide is heated to 240° C. and passed through the bed of the first converter stage at 450 p.s.i.g. and 5,000 space velocity. The temperature of the resulting methanation reaction product is 770° C. and the equilibrium gas composition is 12.5% carbon monoxide, 4% carbon dioxide, 53% hydrogen, 17% methane and 13.5% water vapor.

The effluent gas is passed through a heat recovery unit (steam boiler) where the gas is cooled to 275° C. The cooled gas is passed into the second methanation unit at an inlet temperature of 250° C., where a temperature rise of about 435° C. is encountered to reach 685° C. hot-spot temperature. The effluent gas having reached equilibrium conditions at 685° C. contains 4.2% carbon monoxide, 5.5% carbon dioxide, 37% hydrogen, 33% methane and 20% water. The gas is then passed into a second heat recovery unit and the effluent gas temperature cooled to 245° C.

The gas is next passed into the third methanation unit where a temperature rise of 265° C. is experienced in reaching equilibrium. The effluent gas at 510° C. contains approximately 1% carbon monoxide, 4% carbon dioxide, 25% hydrogen, 37% methane and 33% water vapor. This gas is passed through a heat exchanger to heat the incoming gas to the first converter. This gas can be utilized after water removal as a fuel gas having approximately 700 Btu/ft.$^3$ fuel value or it could be further methanated at a 250° C. inlet and 375° C. outlet to produce a gas having a composition of 0.05% carbon monoxide, 1.75% $CO_2$, 7.5% hydrogen, 47% methane and 44% water vapor, which on removal of water would give a gas having approximately 900 Btu fuel value/ft.$^3$.

The above illustrates the type of converter-catalyst-heat exchanger system for the processing of a theoretical gas having 75% hydrogen and 25% carbon monoxide content. It will be seen that this can be handled to produce a high Btu substitute natural gas in a combination of, e.g., either three or four converters in series to produce different levels of carbon monoxide content in the effluent gas.

In considering another gas stream of 90% hydrogen and 10% carbon monoxide, the gas is first fed to a converter with an inlet temperature of 250° C., 450 psi operating pressure, and charged with a catalyst as described for the first converter in the first paragraph of this example. A temperature rise of approximately 525° C. is experienced and the equilibrium gas composition is about 2% carbon monoxide, 0.03% carbon dioxide, 79% hydrogen, 9.7 methane and 9.5% water vapor. This gas is passed through a heat exchanger (boiler) to lower the temperature to 250° C.

This cooled gas is passed from the heat exchanger to the second converter where a temperature rise of about 160° C. (410° C. hot-spot) is experienced and an equilibrium gas composition of 0.5 ppm carbon monoxide, 0.5 ppm carbon dioxide, 75% hydrogen, 12½% methane and 12½% water vapor is obtained. The catalyst used in this converter is the catalyst of this invention. This gas product after water removal is suitable as a fuel or high quality hydrogen source. After use of the hydrogen for suitable reactions, the unused hydrogen and methane could become a relatively high Btu substitute natural gas.

The foregoing typify gas processing having only two hydrogen and carbon monoxide levels, but serve to illustrate to one knowledgeable in the art the possibilities of a much broader scope of gas compositions.

I claim:

1. A process for methanating carbon oxides contained in a gaseous mixture of 3–25% by volume carbon oxides and hydrogen comprising the sequential steps of
   a. contacting the mixture with a first stage methanation catalyst at a temperature between the threshold and deactivation temperatures of the catalyst by which a partially methanated reaction product is produced having a temperature of 600–900° C.;
   b. cooling the first stage reaction product to 250–450° C.;
   c. contacting the cooled first stage reaction product containing a reduced amount of carbon oxides with at least one intermediate stage methanation catalyst at a temperature between the threshold and deactivation temperature of the catalyst by which further methanated reaction product is produced having a temperature of 450–750° C.;
   d. cooling the intermediate stage reaction product to 200–400° C.; and
   e. contacting the cooled intermediate stage reaction product containing a further reduced amount of carbon oxides with a final stage methanation catalyst at a temperature between the threshold and deactivation temperatures of the catalyst by which an essentially carbon oxide-free reaction product is produced having a temperature of 375–600° C. the process being further characterized in that the temperature of the reaction product from any catalyst stage is higher than for any succeeding stage and at least the final stage methanation catalyst was prepared by the steps
   (1) preparing an aqueous solution of compounds of the metals nickel and chromium in which solution the mol ratio of nickel to chromium is from about 0.5 to about 5.0;
   (2) adjusting the pH of the aqueous solution by which the metals are coprecipitated and separated from solution in finely divided solid form;
   (3) calcining and particulating the coprecipitated solids by which they are converted to an incipient crystalline compound containing a minor amount of hexavalent chromium ions; and
   (4) reducing the hexavalent chromium contained in the incipient crystalline compound to trivalent form while maintaining the nickel in an unreduced oxide form.

2. The process of claim 1 in which the catalysts in the first and intermediate reaction stages are independently selected from the group consisting of nickel chromite, nickel oxide-nickel aluminate, supported nickel oxides and ruthenium.

* * * * *